(12) United States Patent
Py et al.

(10) Patent No.: US 9,951,899 B2
(45) Date of Patent: Apr. 24, 2018

(54) SELF CLOSING CONNECTOR

(71) Applicant: DR. PY INSTITUTE LLC, New Milford, CT (US)

(72) Inventors: Daniel Py, Larchmont, NY (US); Jean-Abraham Py, Larchmont, NY (US)

(73) Assignee: DR. PY INSTITUTE, LLC, New Milford, CT (US)

( * ) Notice: Subject to any disclaimer, the term of this patent is extended or adjusted under 35 U.S.C. 154(b) by 1005 days.

(21) Appl. No.: 13/864,919

(22) Filed: Apr. 17, 2013

(65) Prior Publication Data

US 2013/0270820 A1   Oct. 17, 2013

Related U.S. Application Data

(60) Provisional application No. 61/625,663, filed on Apr. 17, 2012, provisional application No. 61/635,258, (Continued)

(51) Int. Cl.
*F16L 37/24* (2006.01)
*F16L 37/248* (2006.01)
(Continued)

(52) U.S. Cl.
CPC ............ *F16L 37/24* (2013.01); *A61M 5/162* (2013.01); *A61M 39/10* (2013.01); *F16L 37/248* (2013.01);
(Continued)

(58) Field of Classification Search
CPC .......... A61J 1/2065; A61M 2039/0036; A61M 2039/0081; A61M 2039/1072; A61M 2039/267
See application file for complete search history.

(56) References Cited

U.S. PATENT DOCUMENTS 2,304,390 A  12/1942  Wolfram
2,819,914 A   1/1958  Eitner
(Continued)

FOREIGN PATENT DOCUMENTS

CN  101500642 A   8/2009
CN  101584908 A  11/2009
(Continued)

OTHER PUBLICATIONS

International Search Report and Written Opinion of International Searching Authority for International Application No. PCT/US13/36962, dated Aug. 2, 2013.
(Continued)

*Primary Examiner* — Tatyana Zalukaeva
*Assistant Examiner* — Kai Weng
(74) *Attorney, Agent, or Firm* — McCarter & English, LLP

(57) ABSTRACT

An aseptic fluid connector having a male connector and a female connector engageable to aseptically transfer fluid therethrough. The male connector includes a closure and a piercing member comprising a hollow shaft for receiving fluid therein, a tip, and at least one port in fluid communication with the interior of the hollow shaft for passage of the fluid therethrough. The closure and/or the shaft is movable between (i) a first position wherein the closure closes the port(s), and (ii) a second position opening the port(s). The female connector includes a pierceable septum. The male and female connector are engageable such that the piercing member pierces the pierceable septum. Only when the pierceable member has fully penetrated the pierceable septum can the closure and/or the shaft move from the first position, to the second position to aseptically transfer fluid therethrough.

74 Claims, 8 Drawing Sheets

Related U.S. Application Data filed on Apr. 18, 2012, provisional application No. 61/784,764, filed on Mar. 14, 2013.

(51) Int. Cl.

| | |
|---|---|
| *F16L 37/30* | (2006.01) |
| *A61M 39/10* | (2006.01) |
| *A61M 5/162* | (2006.01) |
| *A61M 39/18* | (2006.01) |
| *A61M 39/00* | (2006.01) |
| *A61M 39/26* | (2006.01) |

(52) U.S. Cl.
CPC ............ *F16L 37/30* (2013.01); *A61M 5/1626* (2013.01); *A61M 39/1011* (2013.01); *A61M 39/18* (2013.01); *A61M 2039/0036* (2013.01); *A61M 2039/0081* (2013.01); *A61M 2039/1072* (2013.01); *A61M 2039/267* (2013.01)

(56) References Cited

U.S. PATENT DOCUMENTS

| | | |
|---|---|---|
| 3,367,366 A | 2/1968 | Oliveau |
| 3,692,029 A | 9/1972 | Adair |
| 3,750,667 A | 8/1973 | Pshenichny et al. |
| 3,777,771 A | 12/1973 | De Visscher |
| 3,848,645 A | 11/1974 | Franz |
| 4,052,989 A | 10/1977 | Kline |
| 4,413,985 A | 11/1983 | Wenner et al. |
| 4,421,146 A | 12/1983 | Bond et al. |
| 4,610,469 A | 9/1986 | Wolff-Mooij |
| 4,700,744 A | 10/1987 | Rutter et al. |
| 4,752,292 A | 6/1988 | Lopez et al. |
| 4,756,211 A | 7/1988 | Fellows |
| 4,778,447 A | 10/1988 | Velde et al. |
| 4,778,453 A | 10/1988 | Lopez |
| 4,790,832 A | 12/1988 | Lopez |
| 4,804,015 A | 2/1989 | Albinsson |
| 4,816,024 A | 3/1989 | Sitar et al. |
| 4,846,805 A | 7/1989 | Sitar |
| 4,894,055 A | 1/1990 | Sudnak |
| 4,917,149 A | 4/1990 | Grantham |
| 4,931,048 A | 6/1990 | Lopez |
| 4,938,390 A | 7/1990 | Markva |
| 4,969,870 A | 11/1990 | Kramer et al. |
| 5,049,136 A | 9/1991 | Johnson |
| 5,104,382 A | 4/1992 | Brinkerhoff et al. |
| 5,122,123 A | 6/1992 | Vaillancourt |
| 5,176,643 A | 1/1993 | Kramer et al. |
| 5,199,947 A | 4/1993 | Lopez et al. |
| 5,211,197 A | 5/1993 | Marrison et al. |
| 5,261,891 A | 11/1993 | Brinkerhoff et al. |
| 5,271,744 A | 12/1993 | Kramer et al. |
| 5,279,583 A | 1/1994 | Shober, Jr. et al. |
| 5,281,206 A | 1/1994 | Lopez |
| 5,312,364 A | 5/1994 | Jacobs |
| 5,344,414 A | 9/1994 | Lopez et al. |
| 5,380,306 A | 1/1995 | Brinon |
| 5,387,197 A | 2/1995 | Smith et al. |
| 5,429,256 A | 7/1995 | Kestenbaum |
| 5,451,210 A | 9/1995 | Kramer et al. |
| 5,478,328 A | 12/1995 | Silverman et al. |
| 5,482,083 A | 1/1996 | Jenski |
| 5,492,147 A | 2/1996 | Challender et al. |
| 5,520,666 A | 5/1996 | Choudhury et al. |
| 5,531,692 A | 7/1996 | Rogers |
| 5,549,577 A | 8/1996 | Siegel et al. |
| 5,575,804 A | 11/1996 | Yoon |
| 5,584,848 A | 12/1996 | Yoon |
| 5,607,439 A | 3/1997 | Yoon |
| 5,645,556 A | 7/1997 | Yoon |
| 5,669,891 A | 9/1997 | Vaillancourt |
| 5,685,852 A | 11/1997 | Turkel et al. |
| 5,694,686 A | 12/1997 | Lopez et al. |
| 5,713,874 A | 2/1998 | Ferber |
| 5,810,768 A | 9/1998 | Lopez |
| 5,810,792 A | 9/1998 | Fangrow, Jr. et al. |
| 6,032,691 A | 3/2000 | Powell et al. |
| 6,041,805 A | 3/2000 | Gydesen et al. |
| 6,071,270 A | 6/2000 | Fowles et al. |
| 6,079,444 A | 6/2000 | Harris et al. |
| 6,113,068 A | 9/2000 | Ryan |
| 6,113,583 A | 9/2000 | Fowles et al. |
| 6,135,150 A | 10/2000 | Powell et al. |
| 6,135,167 A | 10/2000 | Kiholm |
| 6,183,442 B1 | 2/2001 | Athanasiou et al. |
| 6,245,048 B1 | 6/2001 | Fangrow, Jr. et al. |
| 6,299,131 B1 | 10/2001 | Ryan |
| 6,394,992 B1 | 5/2002 | Sjoholm |
| 6,409,304 B1 | 6/2002 | Taylor |
| 6,428,520 B1 | 8/2002 | Lopez et al. |
| 6,478,775 B1 | 11/2002 | Galt et al. |
| 6,497,686 B1 | 12/2002 | Adams et al. |
| 6,554,146 B1 | 4/2003 | DeGroff et al. |
| 6,599,273 B1 | 7/2003 | Lopez |
| 6,604,561 B2 | 8/2003 | Py |
| 6,685,674 B2 | 2/2004 | Douglas et al. |
| 6,695,817 B1 | 2/2004 | Fangrow, Jr. |
| 6,726,672 B1 | 4/2004 | Hanly et al. |
| 6,866,158 B1 | 3/2005 | Sommer et al. |
| 6,837,878 B2 | 6/2005 | Smutney et al. |
| 6,989,003 B2 | 1/2006 | Wing et al. |
| 6,994,315 B2 | 2/2006 | Ryan et al. |
| 7,032,631 B2 | 4/2006 | Py |
| 7,077,176 B2 | 7/2006 | Py |
| 7,099,731 B2 | 8/2006 | Lopez |
| 7,100,646 B2 | 9/2006 | Py et al. |
| 7,156,826 B2 | 1/2007 | Ishii et al. |
| 7,174,914 B2 | 2/2007 | Doishi et al. |
| 7,309,326 B2 | 12/2007 | Fangrow, Jr. |
| 7,354,427 B2 | 4/2008 | Fangrow |
| 7,507,227 B2 | 3/2009 | Fangrow |
| 7,510,547 B2 | 3/2009 | Fangrow |
| 7,510,548 B2 | 3/2009 | Fangrow |
| 7,513,895 B2 | 4/2009 | Fangrow |
| 7,534,239 B1 | 5/2009 | Fangrow |
| 7,547,300 B2 | 6/2009 | Fangrow |
| 7,568,509 B2 | 8/2009 | Py |
| 7,569,043 B2 | 8/2009 | Fangrow |
| 7,645,271 B2 | 1/2010 | Fangrow |
| 7,648,491 B2 | 1/2010 | Rogers |
| 7,654,995 B2 | 2/2010 | Warren et al. |
| 7,658,733 B2 | 2/2010 | Fang Row |
| 7,670,322 B2 | 3/2010 | Fangrow, Jr. |
| 7,758,566 B2 | 7/2010 | Simpson et al. |
| 7,824,393 B2 | 11/2010 | Fangrow |
| 7,883,499 B2 | 2/2011 | Fangrow |
| 7,892,216 B2 | 2/2011 | Fangrow, Jr. |
| 7,921,875 B2 | 4/2011 | Moriiki et al. |
| 7,931,615 B2 | 4/2011 | Fangrow, Jr. |
| 8,105,314 B2 | 1/2012 | Fangrow, Jr. |
| 8,196,606 B2 | 6/2012 | Kitagawa |
| 8,246,578 B2 | 8/2012 | Matsumoto |
| 8,348,881 B2 | 1/2013 | Aubert et al. |
| 8,409,164 B2 | 4/2013 | Fangrow |
| 8,454,579 B2 | 6/2013 | Fangrow, Jr. |
| 8,522,832 B2 | 9/2013 | Lopez et al. |
| 8,535,279 B2 | 9/2013 | Schweikert et al. |
| 8,552,832 B2 | 9/2013 | Lopez et al. |
| 8,647,310 B2 | 2/2014 | Fangrow, Jr. et al. |
| 8,696,625 B2 | 4/2014 | Carrel et al. |
| 8,758,306 B2 | 6/2014 | Lopez et al. |
| 8,759,306 B2 | 6/2014 | Lopez et al. |
| 8,808,200 B2 | 8/2014 | Miller et al. |
| 8,956,330 B2 | 2/2015 | Fangrow, Jr. |
| 2002/0032433 A1 | 3/2002 | Lopez |
| 2002/0120212 A1 | 8/2002 | Ritchart et al. |
| 2002/0188260 A1 | 12/2002 | Gollobin |
| 2002/0189712 A1 | 12/2002 | Safabash |
| 2003/0032940 A1 | 2/2003 | Doyle |
| 2003/0070726 A1 | 4/2003 | Andreasson et al. |
| 2003/0106610 A1 | 6/2003 | Roos et al. |
| 2003/0216667 A1 | 11/2003 | Viola |
| 2004/0124389 A1 | 7/2004 | Phillips |

(56) References Cited

U.S. PATENT DOCUMENTS

| | | |
|---|---|---|
| 2004/0222224 A1 | 11/2004 | Plester |
| 2004/0256026 A1* | 12/2004 | Py ............... B29C 66/7394 |
| | | 141/329 |
| 2006/0142735 A1* | 6/2006 | Whitley ............ A61M 39/1011 |
| | | 604/537 |
| 2006/0178646 A1 | 8/2006 | Harris et al. |
| 2006/0287639 A1 | 12/2006 | Sharp |
| 2007/0106225 A1 | 5/2007 | Millerd |
| 2007/0225635 A1 | 9/2007 | Lynn |
| 2008/0103487 A1 | 5/2008 | Miyasaka |
| 2008/0197626 A1 | 8/2008 | Coambs et al. |
| 2009/0082725 A1 | 3/2009 | Witowski |
| 2009/0091129 A1 | 4/2009 | Moriiki et al. |
| 2009/0243281 A1 | 10/2009 | Seifert et al. |
| 2009/0292274 A1 | 11/2009 | Guala |
| 2010/0021230 A1 | 1/2010 | Olivier |
| 2010/0108681 A1 | 5/2010 | Jepson et al. |
| 2010/0121305 A1 | 5/2010 | Rogers |
| 2010/0140290 A1 | 6/2010 | Py |
| 2011/0060312 A1* | 3/2011 | Scheurer ............ A61M 5/14244 |
| | | 604/523 |
| 2011/0106046 A1 | 5/2011 | Hiranuma et al. |
| 2011/0186764 A1 | 8/2011 | Takami |
| 2011/0240158 A1 | 10/2011 | Py |
| 2012/0042971 A1 | 2/2012 | Py |
| 2012/0118416 A1 | 5/2012 | Johnson |
| 2012/0220978 A1 | 8/2012 | Lev et al. |
| 2012/0261027 A1 | 10/2012 | Py |
| 2016/0213910 A1 | 7/2016 | Fangrow, Jr. |

FOREIGN PATENT DOCUMENTS

| | | |
|---|---|---|
| EP | 0174011 A2 | 3/1986 |
| EP | 098871 A2 | 3/2000 |
| EP | 2298407 A1 | 3/2011 |
| JP | S6162468 A | 3/1986 |
| JP | 2001526548 A | 12/2001 |
| JP | 2005504609 A | 2/2005 |
| JP | 2006102254 A | 4/2006 |
| JP | 2009240347 A | 10/2009 |
| JP | 2013526399 A | 6/2013 |
| WO | 9505863 | 3/1995 |
| WO | 2009035383 A1 | 3/2009 |
| WO | 2011117283 A2 | 9/2011 |
| WO | 2011146012 A1 | 11/2011 |

OTHER PUBLICATIONS

European Search Report for European Patent Application No. 13777861.9 dated Dec. 1, 2015. 8 pages.

Japanese Office Action for Japanese Patent Application No. 2015-507148. dated Feb. 21, 2017. 7 pages.

\* cited by examiner

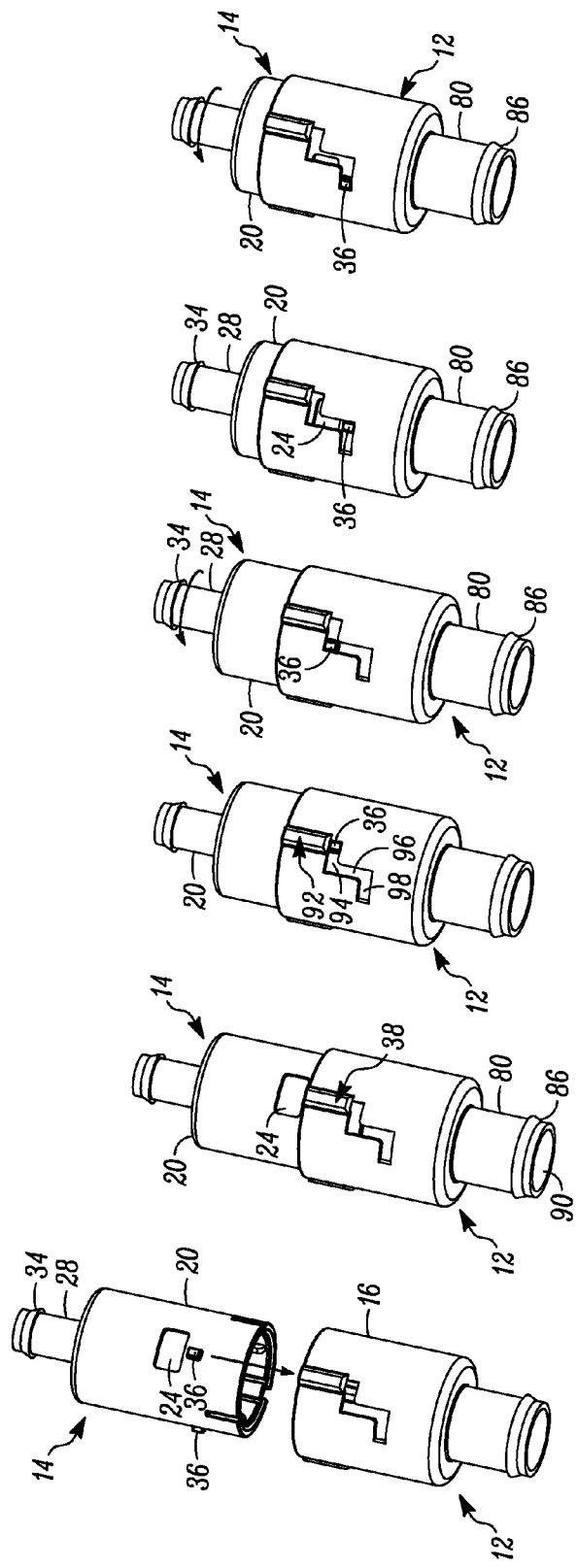

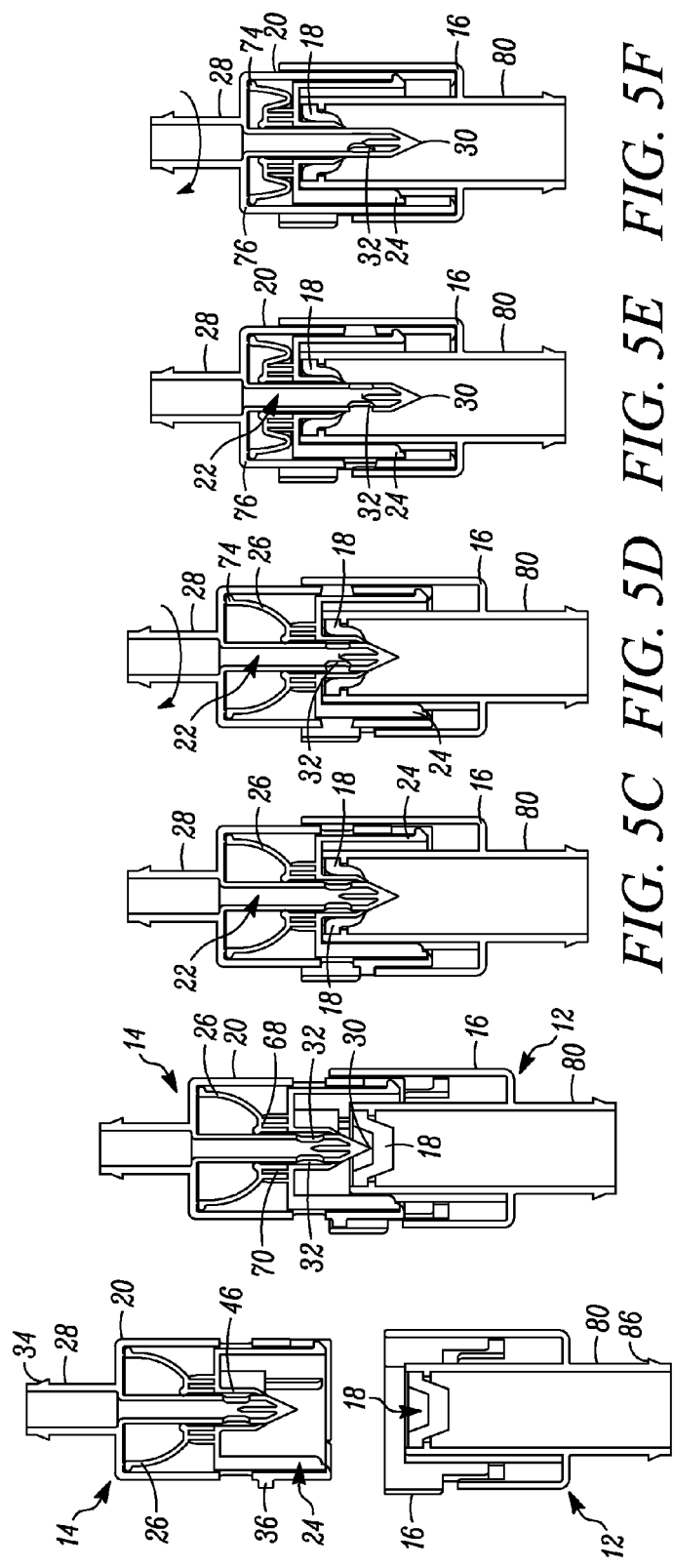

SELF CLOSING CONNECTOR

CROSS-REFERENCE TO RELATED APPLICATION

This patent application claims benefit under 35 U.S.C. § 119 to similarly-titled U.S. Provisional Patent Application Nos. 61/625,663, filed Apr. 17, 2012, 61/635,258, filed Apr. 18, 2012, and 61/784,764, filed Mar. 14, 2013, each of which is hereby incorporated by reference in its entirety as part of the present disclosure.

FIELD OF THE INVENTION

The present invention relates to fluid connectors and methods of transferring fluids, and more particularly, relates to aseptic fluid connectors and methods for aseptically transferring fluids.

BACKGROUND OF THE INVENTION

A typical fluid connector includes a male connector that is received within a female connector to place the two connectors in fluid communication with each other. The male and female connectors may be threadedly engaged, snap fit, or otherwise releasably connected to each other to allow for interconnection and disconnection. Each connector is coupled in fluid communication with a respective fluid passageway, such as a tube or fluid chamber, in order to place the fluid passageways in fluid communication with each other and allow the passage of fluids therebetween.

Such fluid connectors typically do not prevent the contamination of fluids passing through them. For example, prior to interconnection of the male and female connectors, the fluid-contacting surfaces thereof can be exposed to the ambient atmosphere and contaminated through contact with airborne germs and/or by contact with contaminated surfaces. One approach to preventing such contamination is to wipe the fluid-contacting surfaces of the male and female connectors with an alcohol wipe or other disinfectant prior to interconnection. One drawback of this approach is that the fluid-contacting surfaces may become contaminated after the wipe is applied but prior to interconnection of the male and female connectors. Another drawback of this approach is that it can be time consuming and considered a nuisance, and therefore unreliable in practice.

Accordingly, aseptic or sterile fluids can be subjected to contamination when passed through such prior art connectors. Such contamination can give rise to significant problems. If used in a hospital or other medical facility, such as to transfer sterile drugs or other fluids intended for intravenous injection, for example, any such contamination can lead to blood stream infections, serious illnesses, and death by nosocomial infections. In food processing applications, on the other hand, it may be necessary to connect fluid conduits, for example, in order to transfer sterile or aseptic fluids from one passageway to another. If the fluids are contaminated upon passage through a fluid connector, this can lead to contamination of previously-sterile food products, and if such contaminated products are ingested, they can cause infections and/or illnesses. In industrial applications, it may be necessary to prevent a toxic fluid passing through a connector from contaminating the ambient atmosphere, an operator handling the connector, and/or other surfaces that might be located external to the connector. If the fluid-contacting surfaces of the connector are exposed to human contact, or surfaces that come into human contact, for example, this can lead to possible injury and/or illnesses.

SUMMARY OF THE INVENTION

It is an object of the present invention to overcome one or more of the above-described drawbacks and/or disadvantages of the prior art, such as, for example, protecting product flowing through a connector from the environment and the operator and vice versa.

In accordance with a first aspect, a connector comprises a first connector portion including a piercing member comprising a hollow shaft, a tip formed at one end of the shaft, at least one port in fluid communication with the interior of the hollow shaft, and a closure; wherein at least one of the closure and the shaft is movable between (i) a first position wherein the closure closes the at least one port, and (ii) a second position opening the at least one port; a second connector portion adapted to engage the first connector portion and including a pierceable septum configured to be pierced by the piercing member when the first connector portion and the second connector portion are in an engaged position with each other; wherein at least one of the first connector portion and the second connector portion is moveable relative to each other between (i) a closed position wherein the at least one of the closure and the shaft is in the first position and closes the at least one port and (ii) an open position wherein the at least one port has at least partially penetrated through the septum and the at least one of the closure and the shaft is in the second position opening the at least one port.

In some embodiments, the closure forms a substantially fluid-tight seal between the at least one port and the ambient atmosphere when in the first position.

In some embodiments, the closure is biased in the direction from the second position to the first position to normally close the at least one port. In some such embodiments, the needle includes a biasing member, e.g., a spring, biasing the closure in the direction from the second position to the first position. In some such embodiments, the spring is a dome-shaped spring.

In some embodiments, the pierceable septum defines a durometer within the range of about 5 Shore A to about 65 Shore A. In some such embodiments, the pierceable septum defines a durometer within the range of about 25 Shore A to about 50 Shore A.

In some embodiments, the pierceable septum defines a thickness within a range of a thickness equivalent to about ½ the diameter of the piercing member to a thickness equivalent to about double the diameter of the piercing member.

In some embodiments, the tip defines an included angle within the range of about 20 degrees to about 40 degrees. In some such embodiments, the tip defines an included angle of about 30 degrees.

In some embodiment, movement of one of the first connector portion and the second connector portion relative to the other of the first connector portion and the second connector portion from the closed position to the open position achieves at least approximately a 3 log reduction in bio-burden.

In accordance with another aspect, a connector comprises first means for providing fluid to a second means for engaging the first means and for receiving fluid from the first means; the first means comprising third means for providing a conduit for the passage of fluid therethrough; fourth means formed at one end of the third means for piercing a septum;

fifth means in fluid communication with the third means for passage of fluid from the third means therethrough; and sixth means for closing the third means; wherein at least one of the third means and the sixth means is movable between (i) a first position wherein the sixth means closes the fifth means; and (ii) a second position opening the fifth means; the second means comprising seventh means for piercing by the third means when the first means and the second means are in an engaged position with each other; wherein at least one of the first means and the second means is moveable relative to each other between (i) a closed position wherein the at least one of the third means and the sixth means is in the first position and closes the fifth means; and (ii) an open position wherein the fifth means has at least partially penetrated through the seventh means and the at least one of the third means and the sixth means is in the second position opening the fifth means.

In some embodiments, the first means is a first connector portion, the second means is a second connector portion, the third means is a piercing member, the fourth means is a tip of the piercing member, the fifth means is at least one port, the sixth means is a closure, and the seventh means is a pierceable septum.

In accordance with another aspect, a method comprising the following steps:

(i) engaging a first connector portion with a second connector portion, the first connector portion comprising a piercing member comprising a hollow shaft, a tip formed at one end of the shaft, at least one port in fluid communication with the interior of the hollow shaft, and a closure; wherein at least one of the closure and the shaft is movable between (i) a first position wherein the closure closes the at least one port, and (ii) a second position opening the at least one port; wherein the second connector portion is adapted to engage the first connector portion and including a pierceable septum configured to be pierced by the piercing member when the first connector portion and the second connector portion are in an engaged position with each other; and at least one of the first connector portion and the second connector portion is moveable relative to each other between (i) a closed position wherein the at least one of the closure and the shaft is in the first position and closes the at least one port and (ii) an open position wherein the at least one port has at least partially penetrated through the septum and the at least one of the closure and the shaft is in the second position opening the at least one port;

(ii) moving at least one of the first connector portion and the second connector portion relative to each other from the closed position toward the open position;

(iii) piercing the septum with the piercing member and at least partially penetrating through the septum with the at least one port;

(iv) moving at least one of the closure and the shaft from the first position closing the at least one port to the second position opening the at least one port; and (v) introducing fluid from the shaft through the at least one port.

In some embodiments, the step of moving at least one of the closure and the shaft from the first position to the second position occurs after the piercing step.

In some embodiments, the step of moving at least one of the first connector portion and the second connector portion relative to each other comprises both axial and rotational movement.

In some embodiments, the piercing step further comprises wiping the piercing member with the septum. In some such embodiments, the wiping step comprises wiping the tip of the piercing member with the septum. In some such embodiments, the wiping step comprises wiping the piercing member with a septum defining a durometer within the range of about 20 Shore A to about 50 Shore A. In some such embodiments, the wiping step comprises wiping the piercing member with a septum defining a thickness with the range of a thickness equivalent to about ½ the diameter of the piercing member to a thickness equivalent to about double the diameter of the piercing member. In some such embodiments, the wiping step comprises wiping the tip defining an included angle within the range of about 20 degrees to about 40 degrees.

In some embodiments, the piercing, introducing and withdrawing steps are performed in a non-sterile environment or an environment defining a SAL of about 6 log bio-burden on the surface or less; introducing a sterile fluid through the first and second connecting portions; and maintaining the sterility of the filled fluid throughout the piercing, introducing and withdrawing steps.

In accordance with another aspect, the method further comprises the following steps:

(vi) withdrawing the piercing member from the septum;

(vii) before or during the withdrawing step, moving at least one of the closure and the shaft from the second position to the first position (viii) moving the at least one of the first connector portion and the second connector portion relative to each other from the open position to the closed position; and (ix) disengaging the first connector portion with the second connector portion.

One advantage of the present invention is that it provides a closed system sterile transfer, such that product transferred within the system does not come in contact with the external environment. Another advantage of the present invention is that the closure normally closes the piercing member port(s) with respect to ambient atmosphere thereby preventing contamination of the piercing member port and interior of the piercing member and, in turn, preventing contamination of fluid flowing therethrough. The piercing member ports are only opened after the piercing member fully pierces the pierceable septum. Upon withdrawal, the ports are returned to the normally closed position prior, e.g., just before, or during withdrawal. Another advantage of certain embodiments is that the connector aseptically transfers fluid within a non-aseptic, non-sterile or relatively low SAL environment (e.g., about log 6 or lower). Yet another advantage of some embodiments is that the closure is interposed between the piercing member port and a septum to prevent contact between the port and septum, and thereby further prevent any contamination of the port and interior of the needle and of any fluid flowing therethrough.

Other objects and advantages of the present invention, and/or of the currently preferred embodiments thereof, will become more readily apparent in view of the following detailed description and the accompanying drawings.

BRIEF DESCRIPTION OF THE DRAWINGS

FIGS. 4A through 4F are sequential perspective views of the self-closing connector of FIG. 1, showing the male connector from alignment and engagement with the female connector, to full connection with the female connector, for transferring fluid therethrough;

FIGS. 5A through 5F are sequential cross-sectional views of the self-closing connector of FIG. 1, showing the male connector from alignment and engagement with the female connector, to full connection with the female connector, for transferring fluid therethrough;

DETAILED DESCRIPTION OF EMBODIMENTS OF THE INVENTION

Figure 1:
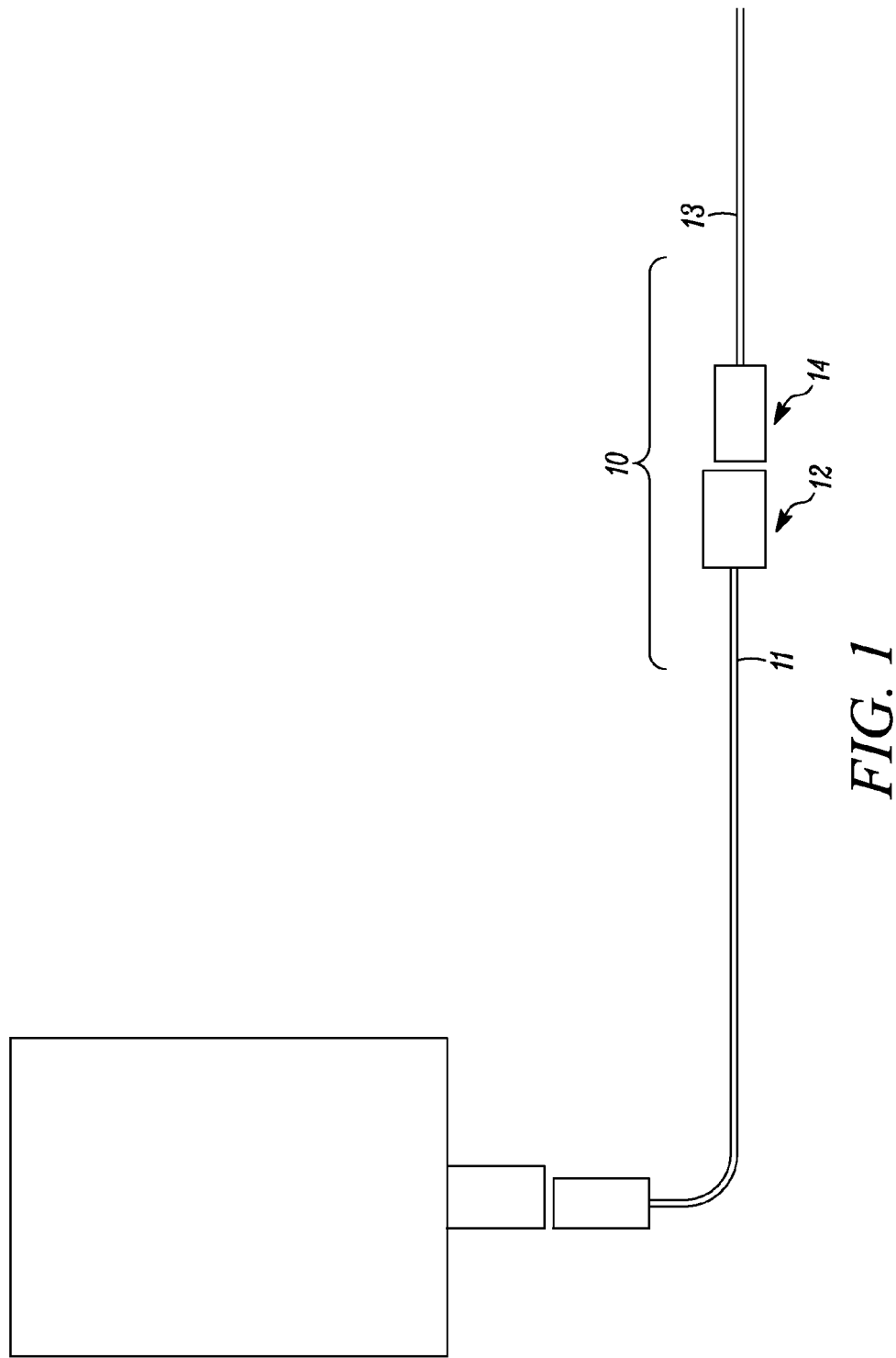
FIG. 1 is a schematic view of a self-closing connector, to transfer fluid from a fluid source.

In FIGS. 1-5, an aseptic self-closing connector is indicated generally by the reference numeral 10. The connector 10 comprises a female or first connector 12 and a male or second connector 14. The male connector 14 comprises a male shell 20 having a piercing member 22, a closure 24, and a spring element 26. The female connector 12 comprises a female shell 16 and a pierceable septum 18. Exemplary pierceable septums are disclosed in the following patents and patent applications which are hereby expressly incorporated by reference as part of the present disclosure: U.S. patent application Ser. No. 08/424,932, filed Apr. 19, 1995, entitled "Process for Filling a Sealed Receptacle under Aseptic Conditions," issued as U.S. Pat. No. 5,641,004; U.S. patent application Ser. No. 09/781,846, filed Feb. 12, 2001, entitled "Medicament Vial Having a Heat-Sealable Cap, and Apparatus and Method for Filling Vial," issued as U.S. Pat. No. 6,604,561, which, in turn, claims priority from U.S. Provisional Patent Application No. 60/182,139, filed Feb. 11, 2000, entitled "Heat-Sealable Cap for Medicament Vial;" U.S. patent application Ser. No. 10/655,455, filed Sep. 3, 2003, entitled "Sealed Containers and Methods of Making and Filling Same," issued as U.S. Pat. No. 7,100,646, which, in turn, claims priority from similarly titled U.S. Provisional Patent Application No. 60/408,068, filed Sep. 3, 2002; U.S. patent application Ser. No. 10/766,172, filed Jan. 28, 2004, entitled "Medicament Vial Having a Heat-Sealable Cap, and Apparatus and Method for Filling the Vial," issued as U.S. Pat. No. 7,032,631, which, in turn claims priority from similarly titled U.S. Provisional Patent Application No. 60/443,526, filed Jan. 28, 2003 and similarly titled U.S. Provisional Patent Application No. 60/484,204, filed Jun. 30, 2003; and U.S. Provisional Patent Application No. 61/625,663, filed Apr. 17, 2012, entitled "Self Closing Connector." However, as may be recognized by those of ordinary skill in the pertinent art based on the teachings herein, the pierceable septum may be made of any of numerous different elastomeric materials, that are currently known or that later become known, such as, for example, silicone.

Figure 3A:
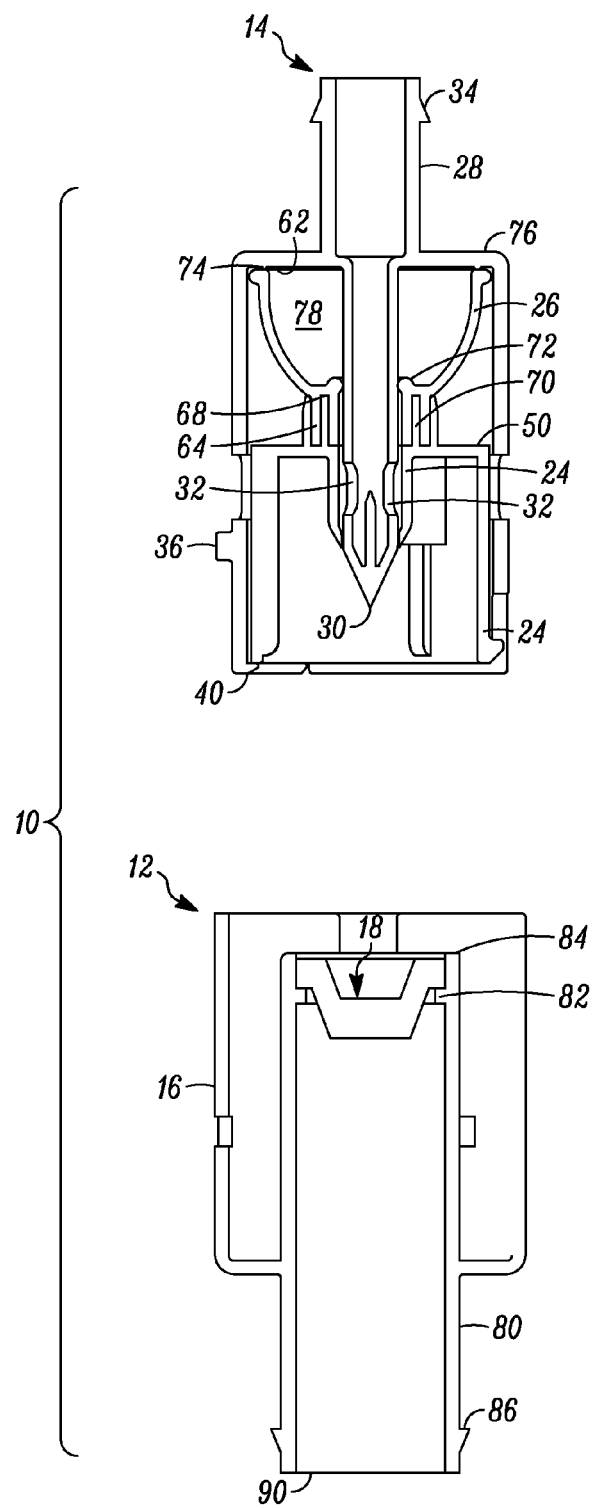
FIG. 3A is a cross-sectional exploded view of the self-closing connector of FIG. 1.

As shown in FIG. 3A, the piercing member 22 comprises a central first hollow shaft 28, with a tip 30 formed at a dispensing end of the shaft, two ports 32, 32, displaced from the tip 30 of the shaft in fluid communication with the interior of the first hollow shaft 28, and a barbed fitting 34 protruding from the hollow shaft at an inlet end thereof, for engaging a fluid line 13 (as shown in FIG. 1). In the illustrated embodiment, the piercing member tip 30 is defined by a non-coring, conically-pointed tip; however, as may be recognized by those of ordinary skill in the pertinent art based on the teachings herein, the tip may define any of numerous other tip configurations that are currently known, or that later become known, such as, for example, a trocar tip. Additionally, the tip may be metal or plastic. For example, the tip can be formed of any of numerous different thermoplastics, including the liquid crystal polymers (LCP) that are highly crystalline, thermotropic (melt-orienting) thermoplastics such as those sold under the trademark Vectra™ by Celanese Corporation, grapheme, or MIM (Metal Injection Molding, such as via the process of Powder Injection Molding). In the illustrated embodiment, the two ports 32 are diametrically opposed relative to each other; however, as may be recognized by those of ordinary skill in the pertinent art based on the teachings herein, the piercing member may define any number of ports that may define any of numerous different configurations and locations. In the illustrated embodiment, the piercing member 22 is integrally molded with the male shell 20; however, as may be recognized by those of ordinary skill in the pertinent art based on the teachings herein, the piercing member may be fixedly attached to the male shell in any of numerous other configurations that currently known, or that later becomes known.

Figures 2A, 2B:
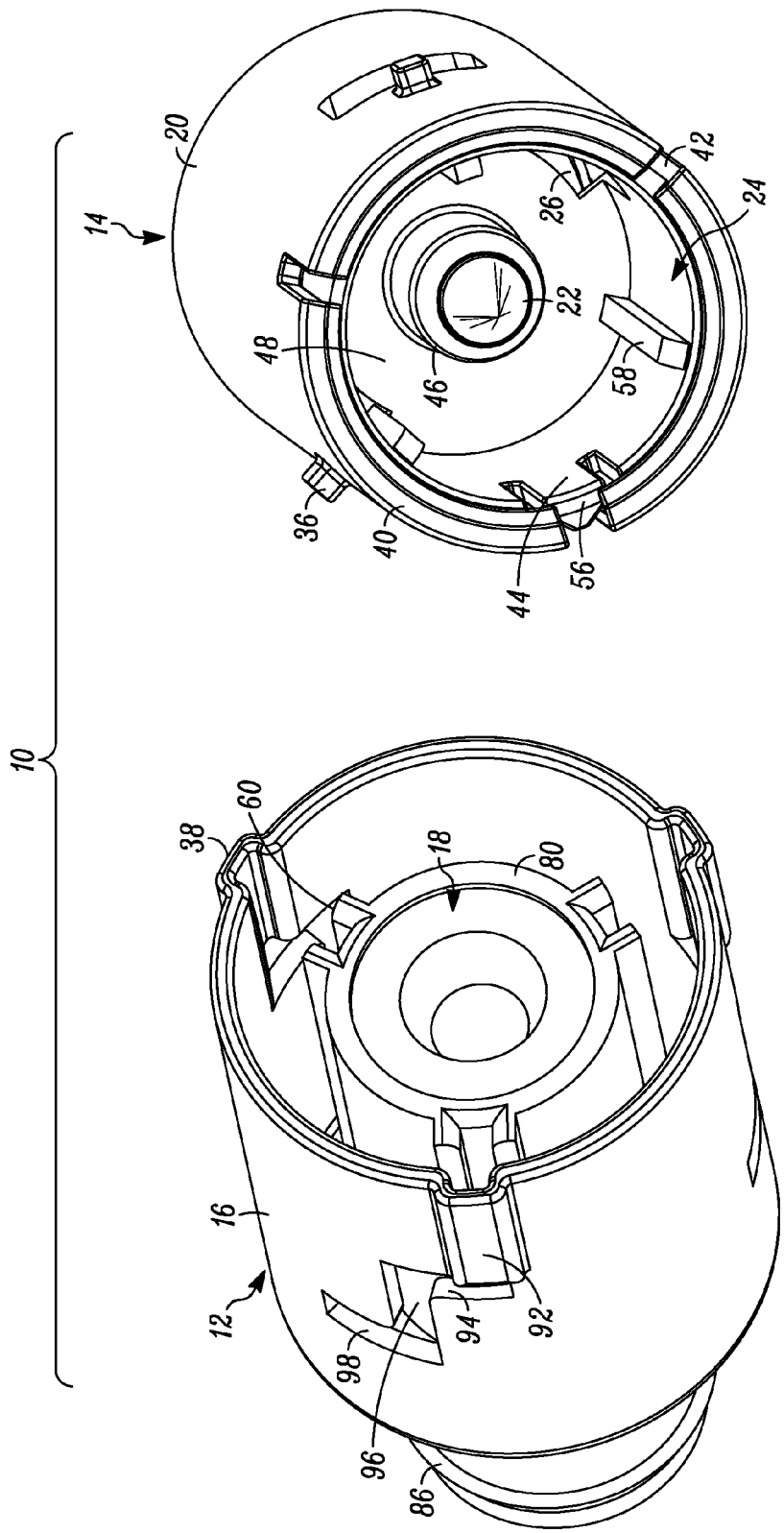
FIG. 2 is an exploded view of the self-closing connector of FIG. 1.

As shown in FIGS. 2-3, the male connector includes lugs 36 laterally extending outwardly from the male shell 20, for engaging corresponding primary receiving slots 38 in the female connector 12, as described further below. The lugs 36 are offset from a distal end 40 of the male connector 14 that engages the female connector 12. The male connector also defines axially-extending slots 42, extending from the distal end 40 of the male connector, as shown in FIG. 2, for receiving therein an alignment tab 44 of the closure 24, as described further below.

In the illustrated embodiment the cylindrical closure 24 is mounted within the cylindrical male shell 20, and includes a central cylindrical shutter 46, axially-extending from a rear wall 48 of the closure. The shutter 46 receives a portion of the piercing member 22 including the ports 32 and extends both annularly and axially thereabout. The closure 24 is both rotatable and axially moveable with respect to the male shell 20. The closure 24 and/or the male shell 20 is axially movable between (i) a first position wherein the shutter 46 closes the ports 32, as shown typically in FIGS. 5A-5D, and (ii) a second position opening the ports 32, as shown typically in FIGS. 5E-5F. In the illustrated embodiment, the shutter 46 forms a substantially fluid-tight seal between the ports 32 and ambient atmosphere when in the closed position. The closure 24, and thus the shutter 46, is biased by a spring element 26 in the direction from the second or open position to the first or closed position to normally close the ports 32, thereby preventing exposure of the ports 32, the interior of the first hollow shaft 28, and any fluid therein to the ambient atmosphere.

The male connector 14 also includes ribs 50, projecting inwardly from the interior wall of the male shell 20 and abutting the rear wall 48 of the closure 24, to normally prevent the closure 24 from moving from the first position toward the second position. The closure 24 includes corresponding slots 52 extending from the rear wall 48 thereof, for receiving said ribs. Only when the ribs 50 align with the slots 52, can the closure 24 axially move from the first position to the second position. The male shell 20 and the closure 24 must first be rotated with respect to one another, in order to align the ribs 50 with the slots 52, as explained further below.

As shown in FIG. 2, the closure 24 also includes the alignment tab 44, integrally formed with and along the cylindrical sidewall 54 of the closure, wherein a distal end 56 of the alignment tab 44 is substantially flush with a distal end of the closure. When the alignment tab 44 engages one of the axially-extending slots 42 of the male shell 20, the closure and the male shell cannot rotate with respect to one another, and therefore the ribs 50 cannot be aligned with the slots 52. However, when the tab 44 is biased inwardly and disengaged from one of the slots 42, as described below, the closure and male shell become rotatable with respect to one another.

The closure 24 also includes axially-extending projections 58, projecting inwardly from the cylindrical side wall 54 of the closure, for engaging secondary receiving slots 60 of the female connector 12, as explained further below. In the illustrated embodiment, the axially-extending projections 58, extend the entire length of the closure sidewall 54, but in other embodiments may not.

Figure 3B:
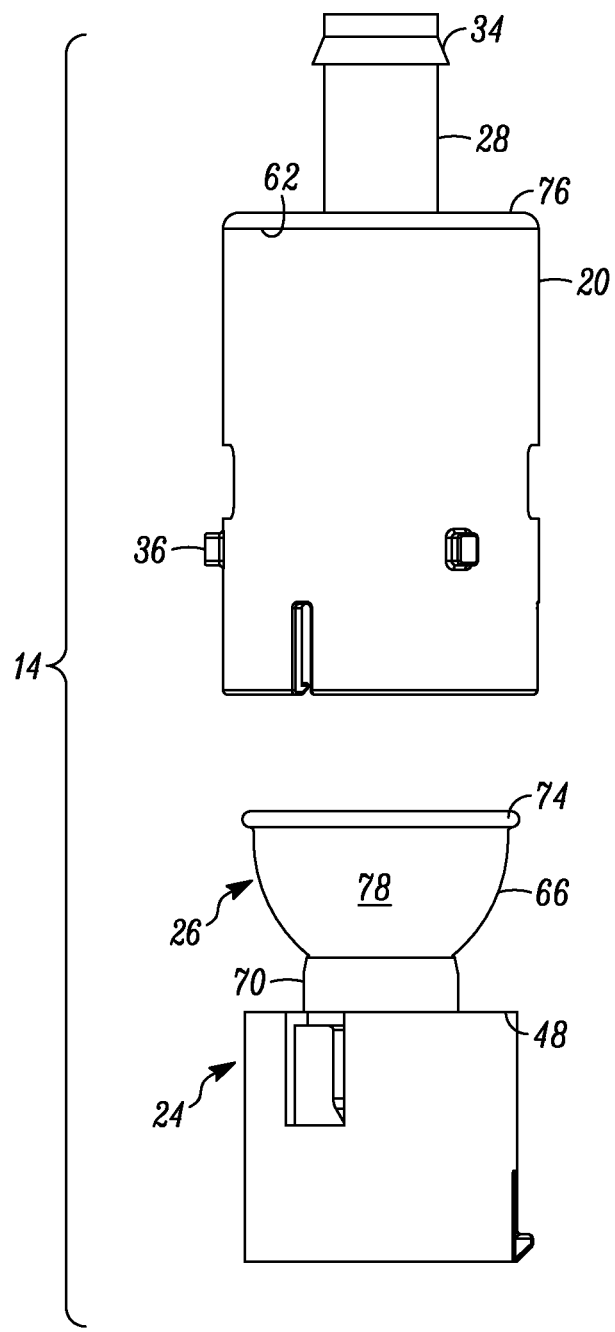
FIG. 3B is a cross-sectional exploded view of the male connector of the self-closing connector of FIG. 1.
Figure 6:
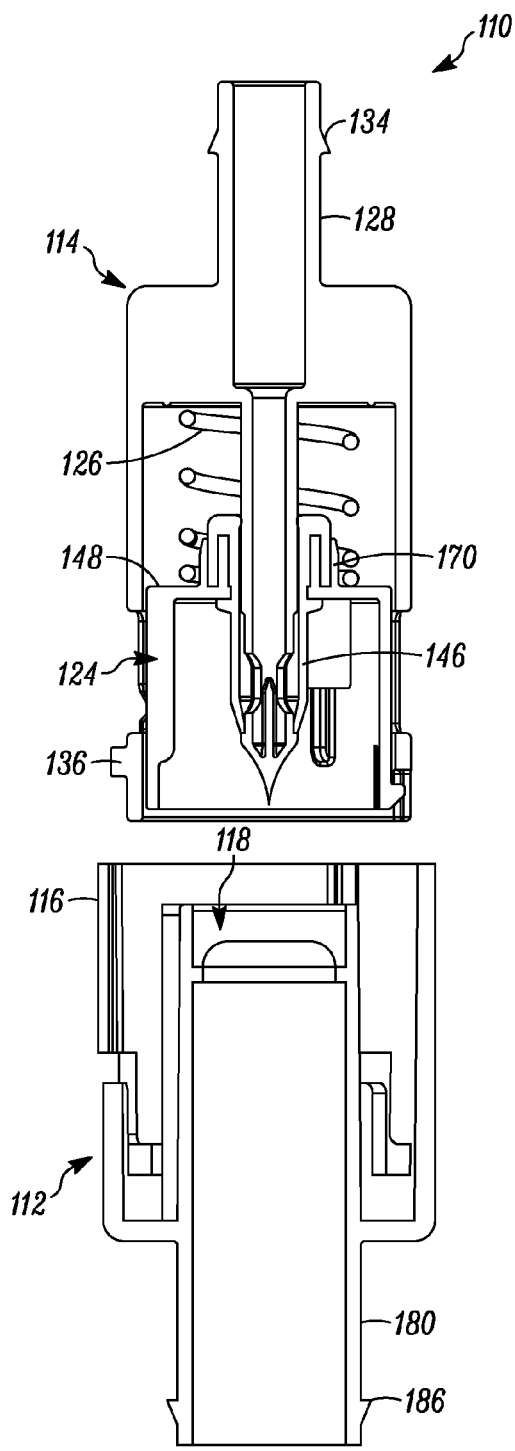
FIG. 6 is a cross-sectional exploded view of another embodiment of a self-closing connector.
Figure 7:
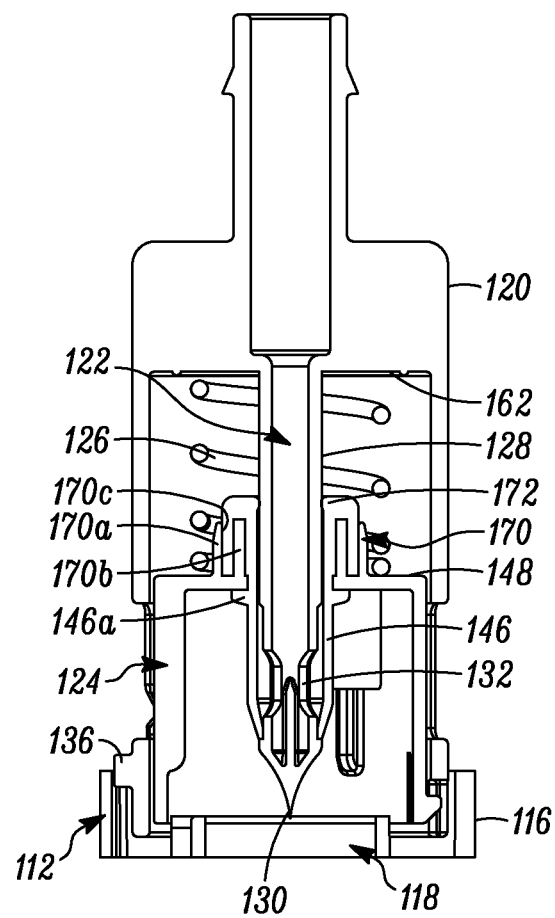
FIG. 7 is an enlarged cross sectional view of the male connector of the self-closing connector of FIG. 6.

In the illustrated embodiment, as shown in FIG. 3B, the male connector 14 includes a substantially dome shaped spring element 26 that naturally biases the closure 24 in the direction from the second or open position to the first or closed position. As may be recognized by those of ordinary skill in the pertinent art based on the teachings herein, the closure may be biased in any of numerous different ways that are currently known or that later become known, and if a spring is used, any of numerous different springs or combinations of springs may be used, such as, for example, a coil spring (FIGS. 6 and 7). As shown in FIG. 3A, the substantially dome shaped spring element 26 is located within the male shell 20, extending between the rear wall 48 of the closure 24 and the rear wall 62 of the male shell 20, and the first hollow shaft 28 of the piercing member 22 extends therethrough. The sprint element 26 comprises a cylindrical portion 64, atop a substantially dome-shaped portion 66. The cylindrical portion includes an annular sealing recess 68, for sealingly receiving a corresponding annular sealing projection 70 extending from the rear wall 48 of the closure 24. In the illustrated embodiment, the spring element 26 is over molded onto the annular sealing projection 70 of the closure 24, to ensure a substantially fluid-tight seal between the cylindrical portion 64 of the spring element and the closure.

The substantially dome-shaped portion 66 of the spring element 26 is formed of a resilient and/or elastomeric material defining an integral spring therein. The integral spring can be manually compressed and maintained in the compressed state. Otherwise, the integral spring naturally rebounds and biases the closure 24 in a direction from the second or open position to the first or closed position. At the junction of the cylindrical portion 64 and the dome-shaped portion 66, the spring element 26 includes an inwardly-extending annular seal 72, sealingly engaging and slideable relative to the first hollow shaft 28 and vice versa. In the illustrated embodiment, the slideable seal is an o-ring, integrally formed with the spring element 26. However, as may be recognized by those of ordinary skill in the pertinent art based on the teachings herein, the slideable seal may take the form of any sealing member, currently known or that later becomes known, capable of sliding along and sealingly engaging the hollow shaft of the piercing member and may not be integral with the spring element.

As shown in FIG. 3B, the opposing base end of the dome-shaped portion 66 includes an integrally formed annular one-way venting valve 74, which engages the rear wall 62 of the male shell 20. The rear wall of the male shell includes corresponding venting holes 76, normally sealed by the valve 74. When the spring element 26 is compressed, the venting valve 74 displaces from the holes 76 due to pressure inside the dome-shaped chamber 78, and allows the venting of air in a single direction out of the chamber 78 of the spring element 26, through the venting holes 76 and to the ambient atmosphere. When the pressure equalizes, the valve 74 resiliently returns to its sealing position on the holes 76. Thereafter, in similar fashion, in order to allow the spring element 26 to naturally rebound and not remain in the compressed position, the venting valve 74 allows the venting of air in a single direction through the venting holes 76, when a vacuum is present in the spring element 26, and into the chamber 78 of the spring element 26. As may be recognized by those of ordinary skill in the pertinent art based on the teachings herein, the one-way venting valve may take the form of any of numerous integral or non-integral valves, that are currently known or that later becomes known, capable of performing the function of the venting valve as described herein.

As shown in FIG. 3A, the female shell 16 comprises a central second hollow shaft 80, or a chamber, within the female shell 16, which receives the pierceable septum 18 therein. In the illustrated embodiment, the second hollow shaft or chamber 80 is integrally molded with the female shell 16; however, as may be recognized by those of ordinary skill in the pertinent art based on the teachings herein, the second hollow shaft may be fixedly attached to the female shell in any of numerous other configurations that currently known, or that later becomes known. The second hollow shaft 80 has an inwardly extending annular seat 82 near an inlet end 84 thereof for sealingly receiving the septum 18 thereon. In the illustrated embodiment, the septum 18 is over molded onto the annular seat 82 to ensure a substantially fluid-tight seal between the septum 18 and the second hollow shaft 80. The second hollow shaft 80 also includes an outwardly extending barbed fitting 86 at an opposing outlet end 90 thereof for connecting to a fluid line 11 (as shown in FIG. 1). As may be recognized by those of ordinary skill in the pertinent art based on the teachings herein, the second hollow shaft my include any of numerous fittings, that are currently known or that later becomes known, for engaging a fluid line.

As shown in FIG. 2, the female shell 16 further includes primary and secondary receiving slots 38, 60, for engaging the lugs 36 of the male shell 20 and the axially-extending projections 58 of the closure 24, respectively. The primary receiving slots 38 are part of the female shell 16 and the secondary receiving slots 60 are formed on the second hollow shaft 80. The secondary receiving slots 60 only extend axially. The primary receiving slots 38, on the other hand, include a first axially-extending portion 92, followed by a first substantially horizontal portion 94, a second axially-extending portion 96, and end with a second substantially horizontal portion 98. The first axially-extending portion 92 consists substantially of an outwardly projecting recess in the female shell wall. Alternatively, the portion 92 could be a window. The first substantially horizontal portion 94, second axially-extending portion 96, and second substantially horizontal portion 98 of the primary receiving slots 38 are formed by windows in the female shell wall. However, the portions 94, 96, and 98 may also be recesses.

As shown in FIGS. 4 and 5, the male and female connectors are connectable for the aseptic transfer of fluid therethrough. First, a male connector 14 and a female connector 12, which may be sterilized, are engaged, as shown typically in FIGS. 4B and 5B. In order to engage the male and female connectors, the alignment tab 44, must first align with one of the primary slots 38, as shown typically in FIGS. 4A and 5A. Otherwise the tab will catch on the edge of the female shell, and prevent engagement. The axially-extending projections 58 of the closure 24 and the lugs 36 of the male shell 22 are configured to also align with the primary and secondary slots 38, 60, respectively, when the alignment tab 44 aligns with one of the primary slots 38. As shown typically in FIGS. 4C and 5C, the male connector 14 is pressed further into engagement with the female connector 12 until the lugs 36 reach the end of the first axially-extending portion 92 of the primary slots 38, and the axially-extending projections 58 reach the end of the secondary slots 60. Because the lugs 36 are offset from the distal end 40 of male shell 20, whereas the alignment tab 44 is substantially flush with the distal end of the closure 24, the alignment tab will reach the end of the first axially-extending portion 92 of the primary slots 38 prior to the lugs 36. Upon reaching this point, the alignment tab 44 is biased inwardly at the first substantially horizontal portion 94, and continues to slide against the inside of sidewall of the female shell 12 until the lugs 36 reach the end of the first axially-extending portion.

As the lugs 36 move down the first axially-extending portion 92 of the primary slots 38, the tip 30 of the piercing member 22 begins to penetrate the pierceable septum 18. As shown typically in FIGS. 5A and 5B, prior to penetrating the septum 18, the shutter 46 is in the closed position and cannot be opened, thereby sealing the ports 32 with respect to ambient atmosphere to maintain the sterility of the ports and of the interior of the piercing member 22. As shown typically in FIG. 5C, upon penetrating the septum 18, the shutter 46 remains in the closed position, and is still interposed between the ports 32 and the septum 18 to substantially prevent contact between the ports and the septum.

The male connector 14 is thereafter rotated to move the lugs 36 along the first substantially horizontal portion 94 of the primary slots 38, as shown typically in FIGS. 4C-4D. Since the secondary slots 60 are solely axially-extending, and the axially-extending projections 58 of the closure 24 are engaged with the secondary slots 60, the closure 24 cannot rotate relative to the female connector 12. However, because the alignment tab 44 of the closure 24 has been inwardly biased, thereby disengaging the tab from the corresponding axially-extending slot 42 of the male shell 20, the male shell is rotatable relative to the closure 24. Consequently, the male shell, along with the piercing member 22, rotates with respect to the stationary closure. Since the piercing member 22 is only rotated in this step, and not moved further axially, the shutter 46 remains in the closed position, continuing to seal the ports 32 with respect to ambient atmosphere and to maintain the sterility of the ports and of the interior of the piercing member 22.

Upon rotation to the end of the first substantially horizontal portion 94 of the primary slots 38, the ribs 50 of the male shell 20 and the corresponding slots 52 extending from the rear wall 48 of the closure 24 align. Only then can the closure and/or the male shell be moved relative to one another to move the ports 32 into the second or open position. The male connector 14 is thus pressed into further axial engagement with the female connector 12, and the lugs 36 move down the second axially-extending portion 96, as shown typically in FIGS. 4D and 4E. Since the axially-extending projections 58 of the closure 24 have already reached the end of the secondary slots 60, the closure is prevented from further axial movement relative to the septum 18. Consequently, as the male shell 20 moves further into engagement with the female connector 12, as shown in FIG. 5E, the piercing member 22 further penetrates the septum 18, while the closure 24 remains in place and compresses spring element 26, to, in turn, move the ports 32 past the end of the closure 42 into the second or open position. As the ports are now past the septum, the septum seals the ports from the ambient atmosphere.

Upon reaching the end of the second axially-extending portion 96 of the primary slots 38, the male connector 14 is rotated again to slide the lugs 36 along the second substantially horizontal portion 98 of the primary slots, as shown typically in FIGS. 4E-4F, to releasably lock the male and female connectors with the ports 32 in the second or open position, i.e., cannot be withdrawn. Alternatively, the portion 98 may not be present. In the open position of FIGS. 5E and 5F, fluid may travel from a fluid line, through the first hollow shaft 28 of the piercing member 22, through the open ports 32, and into the second hollow shaft 80 of the female connector 12. Since the sterile ports 32 are never exposed to the ambient atmosphere, the ports, interior of the piercing member, and fluid flowing therethrough, are not contaminated and/or are maintained sterile as the fluid passes therethrough to the female connector 12.

To disconnect the male and female connectors 14, 12, the connecting steps are generally reversed. First, the male connector 14 is rotated to slide the lugs 36 in the reverse direction along the second substantially horizontal portion 98 (if present) of the primary slots 38, thereby unlocking the ports 32 from the open position. Upon reaching the opposing end of the second substantially horizontal portion and subsequent movement along portion 96, the spring element 26 naturally rebounds and returns the ports 32 from the open position into the normally closed position, wherein the ports are again sealingly covered by the shutter 46. The shutter 46 remains interposed between the ports 32 and the septum 18 and therefore substantially prevents contact between the ports and the septum. The closed position is thereafter maintained, e.g., by the bias of the spring element 26 throughout the remainder of the disconnection process. The lugs 36 are also moved back up the second axially-extending portion 96 of the primary slots 38 with the natural rebound of the sprint element 26. Thereafter, the male connector 14 is rotated to move the lugs 36 along the first substantially horizontal portion 94 of the primary slots 38, returning the male connector 14 to its original configuration. The male connector 14 is then pulled out of engagement from the female connector 12, thereby withdrawing the tip 30 of the piercing member 22 from the septum 18 and withdrawing the lugs 36 and the axially-extending projections 58 from the first axially-extending portion of the primary slots 38 and the secondary slots 60, respectively. The shutter 46 remains closed over the ports 32 and prevents contact between the ports and the septum 18 during withdrawal therefrom. Thus, during, and upon, and in some embodiments, before, withdrawal of the piercing member 22 from the septum 18, the shutter 46 maintains the ports 32 in the closed position and cannot be opened, thereby preventing any contamination of the ports or interior of the piercing member.

In some embodiments, the septum 18 is engineered to self-close and thereby ensure that the head loss left by the residual piercing aperture after the tip 30 of the piercing member 22 is withdrawn prevents any fluid ingress therethrough. Nonetheless, although the septum 18 is self-closing, the resulting piercing aperture in the septum may be resealed mechanically (such as by an overlying cover (not shown)), by applying a liquid sealant thereto, e.g., a silicone or silicon-based sealant, or by applying radiation or energy thereto, e.g., laser or thermal, or light, e.g., UV or ultraviolet light or radiation, in the case of a light or UV cured liquid sealant, to form a fluid tight or hermetic seal and thereby maintain the sterility of the transferred fluid, in accordance with the teachings of the inventor's U.S. Provisional Patent Application No. 61/686,867, entitled "Modular Filling Apparatus and Method," filed Apr. 13, 2012, and U.S. patent application Ser. No. 12/901,420, entitled "Device with Co-Molded Closure, One-Way Valve and Variable Volume Storage Chamber and Related Method," filed Oct. 8, 2010, which, in turn, claims priority to similarly titled U.S. Provisional Patent Application No. 61/250,363, filed Oct. 9, 2009, which are hereby incorporated by reference in their entireties as part of the present disclosure.

The process may then be repeated whereby the male and female connectors are re-connected to aseptically transfer fluid therethrough once again. In some embodiments, the tip 30 of the piercing member 22 may be re-sterilized prior to repeating connection of the two connectors to ensure that the tip does not introduce contaminants into the sterile interior of the second hollow shaft 80. Sterilization and re-sterilization of the male and female connectors and/or any component parts therein may be achieved in accordance with the teachings of any of the patents and patent applications previously incorporated by reference above.

In some embodiments, the septum 18 comprises a lower, i.e., base, high durometer layer and an upper relatively lower durometer layer. In some such embodiments, the upper layer is not bondable with the lower layer and is over-molded thereon. In some such embodiments, the septum 18 may wipe the tip 30 of the piercing member 22 and the shutter 24 of contaminants thereon during engagement and penetration of the septum 18 by the tip 30, to prevent the tip and/or shutter from introducing such contaminants into the sterile interior of the second hollow shaft 80 of the female connector 12. The effectiveness of such wiping during piercing of the septum is dependent upon several factors, such as, the wall thickness and durometer of the septum as well as the included angle of the tip of the piercing member. In some embodiments, the durometer of the septum 18, or the layers thereof, is within the range of about 5 Shore A to about 65 Shore A, such as, for example, within the range of about 20 Shore A to about 50 Shore A. In some such embodiments, the durometer of the septum 18 is within the range of about 25 Shore A to about 45 Shore A. In some such embodiments the septum thickness is within the range of about ½ the diameter of the piercing member to about double the largest diameter of the piercing member. In yet some such embodiments, the included angle of the tip of the piercing member is within the range of about 20 degrees to about 40 degrees, such as about 30 degrees. The present inventor has determined that the wiping effect on a tip surface by a septum having a wall thickness and durometer as well as the included angle of the tip of a piercing member within said aforementioned ranges may achieve at least approximately a 3 log reduction in bio-burden when the male and female connectors are connected while immersed in a broth, which is about the reduction achieved by known UV pulse (5 second) sterilization techniques, to thereby at least partially sterilize the tip surface. Therefore, one advantage of the present invention is that it allows substantially sterile transfer of fluids within a non-aseptic, non-sterile or relatively low sterility assurance level ("SAL") environment (e.g., about 6 log bioburden or lower).

In FIGS. 6-7, another connector is indicated generally by the reference numeral 110. The connector 110 is substantially similar to the connector 10 described above in connection with FIGS. 1-5, and therefore like reference numerals preceded by the numeral "1" are used to indicate like elements. A primary difference of the connector 110 in comparison to the connector 10 is that the spring element 126 of the male connector 114 is a coil spring. Additionally, the central cylindrical shutter 146 and the closure 124 define two parts, rather than one part.

As shown in FIG. 7, the closure 124 includes an annular sealing projection 170 extending from the rear wall 148 thereof. The annular sealing projection comprises an outer annular wall 170a and an inner annular wall 170b having a smaller diameter than the outer wall. The outer and inner walls 170a, 170b define an annular channel 170c therebetween. The proximal end of the shutter 146 mounts onto the projection 170, i.e., engages with the annular channel 170c, and extends into the closure 124 to the proximal end of the piercing member 122, thereby sealing the ports 132. As shown in FIG. 7, the shutter 146 also includes an inwardly-extending annular seal 172 at the proximal ends thereof, sealingly engaging the first hollow shaft 128. The shutter 146 includes an annular projection 146a laterally extending therefrom and abutting the interior surface of the rear wall 148 of the closure 124. Thus, the shutter 146 is securely mounted to the closure 124.

The closure 124 and shutter 146 being two different parts permits the use of different materials for each. Accordingly, the materials for each can be optimized depending upon their function and service. Specifically, a primary function of the closure is structural. A primary function of the shutter 146 is sealing, e.g., the ports 132. In some embodiments, the closure 124 is formed of polypropylene. In some such embodiments, the shutter 146 is formed of a low durometer thermoplastic elastomer, such as, for example, a hardness of approximately 90 shore A. In other such embodiments, the shutter 146 can be formed of a very low density polyethylene.

In the illustrated embodiment, the shutter 146 is over-molded onto the projection 170 of the closure 124. However, as should be understood by those of ordinary skill in the art, the closure 124 and the shutter 146 can be formed to engage with one another in any of numerous different manners currently known or that later become known.

As shown in FIGS. 6 and 7, the spring element 126 is a coil spring. The coil-spring 126 extends between the rear wall 148 of the closure 124 and the rear wall 162 of the male shell 120, and encases the first hollow shaft 128 and the annular projection 160. In the illustrated embodiment, the coil spring formed of a metal. However, as should be understood by those of ordinary skill in the pertinent art, the coil-spring may be formed of any of numerous different materials providing a spring rate sufficient for the spring 126 to perform the functions disclosed herein. Similar to the embodiment of FIGS. 1-5 above, the coil spring 126 biases the closure 124 in a direction from the second or open position to the first or closed position, and is manually compressed when the closure 124 is moved in a direction from the first position toward the second position.

As may be recognized by those of ordinary skill in the pertinent art based on the teachings herein, numerous changes and modifications may be made to the above-described and other embodiments of the present invention without departing from its scope. For example, the male and female connector component parts may be made of any of numerous different metals or plastics that are currently known or that later become known. The term "piercing member" is used herein to mean any of numerous different types of devices that are used to penetrate and introduce matter into an object, that are currently known, or that later become known. The term "septum" is used herein to mean any of numerous different types of penetrable septums, stoppers or other devices that are penetrable by a piercing member. Accordingly, this detailed description of embodiments is to be taken in an illustrative, as opposed to a limiting sense.

What is claimed is:

1. A connector comprising:
   a first connector portion including a piercing member comprising a hollow shaft, a tip formed at one end of the shaft, at least one port in fluid communication with an interior of the hollow shaft, and a closure that receives only a portion of the piercing member including the at least one port; wherein one or more of the closure or the shaft is movable between (i) a first position wherein the closure closes the at least one port, and (ii) a second position opening the at least one port;
   a second connector portion adapted to engage the first connector portion and including a pierceable septum configured to be pierced by the piercing member when the first connector portion and the second connector portion are in an engaged position with each other;
   wherein one or more of the first connector portion or the second connector portion is moveable relative to each other between (i) a closed position wherein the at least one port has at least partially penetrated into or through the septum and the one or more of the closure or the shaft is in the first position and closes the at least one port and (ii) an open position wherein the at least one port has at least partially penetrated into or through the septum and the one or more of the closure or the shaft is in the second position opening the at least one port.

2. A connector as defined in claim 1, wherein in the first position, the closure forms a substantially fluid-tight seal between the at least one port and the ambient atmosphere.

3. A connector as defined in claim 1, wherein the closure is normally biased in the direction from the second position toward the first position to normally close the at least one port.

4. A connector as defined in claim 1, further including a biasing member that normally biases the closure in the direction from the second position to the first position.

5. A connector as defined in claim 4, wherein the biasing member includes a sealing member for sealingly engaging the hollow shaft of the piercing member.

6. A connector as defined in claim 5, wherein the sealing member is integrally formed with the biasing member.

7. A connector as defined in claim 5, wherein the sealing member comprises an O-ring.

8. A connector as defined in claim 4, wherein the biasing member comprises an elastic spring.

9. A connector as defined in claim 8, wherein the elastic spring is approximately dome shaped.

10. A connector as defined in claim 9, wherein the approximately dome shaped spring is over-molded to the closure.

11. A connector as defined in claim 9, wherein the first connector portion further includes a one-way valve.

12. A connector as defined in claim 11, wherein the one-way valve is configured to vent out air from the approximately dome shaped spring to the ambient atmosphere, when the one or more of the closure or the shaft is moved from the first position to the second position.

13. A connector as defined in claim 12, wherein the one-way valve is configured to vent in air from the ambient atmosphere into the approximately dome shaped spring, when the one or more of the closure or the shaft is moved from the second position to the first position.

14. A connector as defined in claim 11, wherein the one-way valve is integrally formed with the approximately dome shaped spring.

15. A connector as defined in claim 1, wherein the pierceable septum is elastomeric.

16. A connector as defined in claim 15, wherein the pierceable septum defines a durometer within the range of about 20 Shore A to about 50 Shore A.

17. A connector as defined in claim 16, wherein the pierceable septum defines a durometer within the range of about 25 Shore A to about 45 Shore A.

18. A connector as defined in claim 16, wherein the pierceable septum defines a thickness within the range of a thickness equivalent to about ½ the diameter of the piercing member to a thickness equivalent to about double the diameter of the piercing member.

19. A connector as defined in claim 1, wherein the tip defines an included angle within the range of about 20 degrees to about 40 degrees.

20. A connector as defined in a claim 19, wherein the tip defines an included angle of about 30 degrees.

21. A connector as defined in claim 1, wherein movement of one of the first connector portion and the second connector portion relative to the other of the first connector portion and the second connector portion from the closed position to the open position achieves at least approximately a 3 log reduction in bio-burden.

22. A connector as defined in claim 1, wherein the closure of the first connector portion is engageable with a portion of the second connector portion to prevent further movement of the closure relative thereto, whereby subsequent movement of the first connector portion moves the shaft from the first position to the second position.

23. A connector as defined in claim 1, wherein one or more of the closure or the shaft is movable from the second position, wherein the at least one port is opened, to the first position, wherein the at least one port is closed and sealed with respect to ambient atmosphere, during or upon withdrawing the piercing member from the septum.

24. A connector as defined in claim 1, wherein the closure includes a shutter extending annularly about the shaft.

25. A connector as defined in claim 1, wherein the first connector portion further includes at least one lug, and the second connector portion further includes at least one corresponding slot, wherein the at least one lug is adapted to engage the at least one slot to rotationally align the first and second connector portions with one another.

26. A connector as defined in claim 1, wherein the tip of the piercing member is defined by a non-coring, conically-pointed tip.

27. A connector as defined in claim 1, further comprising a fitting adjacent an end of the shaft opposite the tip and engageable in fluid communication with a filling line for introducing fluid from the filling line through the connector.

28. A connector comprising:
   first means for providing fluid to a second means for engaging the first means and for receiving fluid from the first means;
   the first means comprising
      third means for providing a conduit for the passage of fluid therethrough;
      fourth means formed at one end of the third means for piercing a septum;
      fifth means in fluid communication with the third means for passage of fluid from the third means therethrough; and sixth means for receiving only a portion of the third means, including the fifth means, and for closing the third means;

wherein one or more of the third means or the sixth means is movable between
 (i) a first position wherein the sixth means closes the fifth means; and
 (ii) a second position opening the fifth means;

the second means comprising
 seventh means for piercing by the third means when the first means and the second means are in an engaged position with each other;

wherein one or more of the first means or the second means is moveable relative to each other between
 (i) a closed position wherein the fifth means has at least partially penetrated into or through the seventh means and the one or more of the third means or the sixth means is in the first position and closes the fifth means; and
 (ii) an open position wherein the fifth means has at least partially penetrated into or through the seventh means and the one or more of the third means or the sixth means is in the second position opening the fifth means.

29. A connector as defined in claim 28, wherein the first means is a first connector portion, the second means is a second connector portion, the third means is a piercing member, the fourth means is a tip of the piercing member, the fifth means is at least one port, the sixth means is a closure, and the seventh means is a pierceable septum.

30. A method comprising:
 engaging a first connector portion with a second connector portion,
 the first connector portion comprising a piercing member including a hollow shaft, a tip formed at one end of the shaft, at least one port in fluid communication with an interior of the hollow shaft, and a closure that receives only a portion of the piercing member including the at least one port; wherein one or more of the closure or the shaft is movable between (i) a first position wherein the closure closes the at least one port, and (ii) a second position opening the at least one port;
 the second connector portion is adapted to engage the first connector portion and including a pierceable septum configured to be pierced by the piercing member when the first connector portion and the second connector portion are in an engaged position with each other;
 and one or more of the first connector portion or the second connector portion is moveable relative to each other between (i) a closed position wherein the at least one port has at least partially penetrated into or through the septum and the one or more of the closure or the shaft is in the first position and closes the at least one port and (ii) an open position wherein the at least one port has at least partially penetrated into or through the septum and the one or more of the closure or the shaft is in the second position opening the at least one port;
 moving one or more of the first connector portion or the second connector portion relative to each other from the closed position toward the open position;
 piercing the septum with the piercing member and at least partially penetrating into or through the septum with the at least one port;
 moving one or more of the closure or the shaft from the first position, closing the at least one port, to the second position, opening the at least one port; and
 introducing fluid from or into the shaft through the at least one port.

31. A method as defined in claim 30, wherein the step of moving one or more of the closure or the shaft from the first position to the second position occurs after the piercing step.

32. A method as defined in claim 30, wherein the fluid is introduced from or into the shaft through the at least one port after full perforation of the septum or after part of the at least one port has passed through an interior surface of the septum and is located within a hollow shaft of the second connector portion.

33. A method as defined claim 30, further comprising substantially sealing the at least one port from ambient atmosphere in the closed position.

34. A method as defined in claim 30, further comprising the step of sterilizing the first connector portion and the second connector portion.

35. A method as defined in claim 30, further comprising the step of aligning the first connector portion with the second connector portion.

36. A method as defined in claim 30, wherein the step of moving one or more of the first connector portion or the second connector portion relative to each other comprises both axial and rotational movement.

37. A method as defined in claim 30, wherein the piercing step further comprises wiping contaminants from the piercing member with the septum.

38. A method as defined in claim 37, wherein the wiping step comprises wiping the tip of the piercing member with the septum.

39. A method as defined in claim 37, wherein the wiping step comprises wiping the piercing member with a septum defining a durometer within the range of about 20 Shore A to about 50 Shore A.

40. A method as defined in claim 39, wherein the wiping step comprises wiping the piercing member with a septum defining a durometer within the range of about 25 Shore A to about 45 Shore A.

41. A method as defined in claim 39, wherein the wiping step comprises wiping the piercing member with a septum defining a thickness with the range of a thickness equivalent to about ½ the diameter of the piercing member to a thickness equivalent to about double the largest diameter of the piercing member.

42. A method as defined claim 38, wherein the wiping step comprises wiping the tip defining an included angle within the range of about 20 degrees to about 40 degrees.

43. A method as defined in claim 42, wherein the wiping step comprises wiping the tip defining an included angle of about 30 degrees.

44. A method as defined in claim 37, wherein the wiping step achieves at least approximately a 3 log reduction in bio-burden of the piercing member.

45. A method as defined in claim 30, further comprising the following steps:
 withdrawing the piercing member from the septum;
 before or during the withdrawing step, moving one or more of the closure or the shaft from the second position to the first position, such that the at least one port is in the closed position and sealed with respect to ambient atmosphere;
 moving the one or more of the first connector portion or the second connector portion relative to each other from the open position to the closed position; and
 disengaging the first connector portion with the second connector portion.

46. A method as defined in claim 45, further including, during the piercing and withdrawing steps, substantially preventing any contact between the at least one port and the septum.

47. A method as defined in claim 45, further comprising interposing the closure between the at least one port and septum to substantially prevent any contact between the at least one port and septum.

48. A method as defined in claim 45, further comprising performing the piercing, introducing and withdrawing steps in a non-sterile environment or an environment defining a SAL of about log 3 or less; introducing a sterile fluid through the first and second connector portions; and maintaining the sterility of the filled fluid throughout the piercing, introducing and withdrawing steps.

49. A method as defined in claim 45, wherein the septum is self-closing and substantially prevents the ingress of fluid through the resulting penetration aperture.

50. A connector as in claim 1, wherein the septum is configured to wipe contaminants from the piercing member during movement of one of the first connector portion and the second connector portion relative to the other of the first connector portion and the second connector portion.

51. A connector as in claim 50, wherein the wiping achieves at least approximately a 3 log reduction in bioburden.

52. A connector as in claim 1, wherein the closure does not receive the tip in the first position and the second position.

53. A connector as in claim 1, wherein the tip extends distally beyond the closure in the first position.

54. A connector as in claim 28, wherein the sixth means does not receive the fourth means in the first position and the second position.

55. A connector as in claim 28, wherein the fourth means extends distally beyond the sixth means in the first position.

56. A method as in claim 30, wherein the closure does not receive the tip in the first position and the second position.

57. A method as in claim 30, wherein the tip extends distally beyond the closure in the first position.

58. A connector comprising:
a first connector portion including a piercing member comprising a hollow shaft, a tip formed at one end of the shaft, at least one port in fluid communication with an interior of the hollow shaft, and a closure that receives only a portion of the piercing member including the at least one port; wherein one or more of the closure or the shaft is movable between (i) a first position wherein the closure closes the at least one port, and (ii) a second position opening the at least one port;
a second connector portion adapted to engage the first connector portion and including a pierceable septum configured to be pierced by the piercing member when the first connector portion and the second connector portion are in an engaged position with each other;
wherein one or more of the first connector portion or the second connector portion is moveable relative to each other between (i) a closed position wherein the one or more of the closure or the shaft is in the first position and closes the at least one port and (ii) an open position wherein the at least one port has at least partially penetrated into or through the septum and the one or more of the closure or the shaft is in the second position opening the at least one port,
wherein the septum is configured to wipe contaminants from the piercing member during movement of one of the first connector portion and the second connector portion relative to the other of the first connector; and
wherein contact between the at least one port and the septum is substantially prevented when the septum is pierced by the piercing member and the second connector portion.

59. A connector as in claim 58, wherein said wiping achieves at least approximately a 3 log reduction in bioburden.

60. A connector as defined in claim 58, wherein the pierceable septum defines a durometer within the range of about 20 Shore A to about 50 Shore A.

61. A connector as defined in claim 58, wherein the pierceable septum defines a thickness within a range of a thickness equivalent to about ½ the diameter of the piercing member to a thickness equivalent to about double the diameter of the piercing member.

62. A connector as defined in claim 58, wherein the tip defines an included angle within the range of about 20 degrees to about 40 degrees.

63. A method comprising:
engaging a first connector portion with a second connector portion,
the first connector portion comprising a piercing member including a hollow shaft, a tip formed at one end of the shaft, at least one port in fluid communication with an interior of the hollow shaft, and a closure that receives only a portion of the piercing member including the at least one port; wherein one or more of the closure or the shaft is movable between (i) a first position wherein the closure closes the at least one port, and (ii) a second position opening the at least one port;
the second connector portion is adapted to engage the first connector portion and including a pierceable septum configured to be pierced by the piercing member when the first connector portion and the second connector portion are in an engaged position with each other;
and one or more of the first connector portion or the second connector portion is moveable relative to each other between (i) a closed position wherein the one or more of the closure or the shaft is in the first position and closes the at least one port and (ii) an open position wherein the at least one port has at least partially penetrated into or through the septum and the one or more of the closure or the shaft is in the second position opening the at least one port;
moving one or more of the first connector portion or the second connector portion relative to each other from the closed position toward the open position;
piercing the septum with the piercing member, at least partially penetrating into or through the septum with the at least one port, and, during said piercing, wiping contaminants from the piercing member with the septum;
moving one or more of the closure or the shaft from the first position, closing the at least one port, to the second position, opening the at least one port;
introducing fluid from or into the shaft through the at least one port; and
during the piercing step, substantially preventing any contact between the at least one port and the septum.

64. A method as defined in claim 63, wherein the wiping step comprises wiping the tip of the piercing member with the septum.

65. A method as defined in claim 63, wherein the wiping step comprises wiping the piercing member with a septum defining a durometer within the range of about 20 Shore A to about 50 Shore A.

66. A method as defined in claim 65, wherein the wiping step comprises wiping the piercing member with a septum defining a thickness with the range of a thickness equivalent to about ½ the diameter of the piercing member to a thickness equivalent to about double the largest diameter of the piercing member.

67. A method as defined claim 64, wherein the wiping step comprises wiping the tip defining an included angle within the range of about 20 degrees to about 40 degrees.

68. A method as defined in claim 63, wherein the wiping step achieves at least approximately a 3 log reduction in bio-burden of the piercing member.

69. A method as defined in claim 63, wherein the wiping step achieves at least approximately a 3 log reduction in bio-burden of the piercing member.

70. A method comprising:
   engaging a first connector portion with a second connector portion,
   the first connector portion comprising a piercing member including a hollow shaft, a tip formed at one end of the shaft, at least one port in fluid communication with an interior of the hollow shaft, and a closure that receives only a portion of the piercing member including the at least one port; wherein one or more of the closure or the shaft is movable between (i) a first position wherein the closure closes the at least one port, and (ii) a second position opening the at least one port;
   the second connector portion is adapted to engage the first connector portion and including a pierceable septum configured to be pierced by the piercing member when the first connector portion and the second connector portion are in an engaged position with each other;
   and one or more of the first connector portion or the second connector portion is moveable relative to each other between (i) a closed position wherein the one or more of the closure or the shaft is in the first position and closes the at least one port and (ii) an open position wherein the at least one port has at least partially penetrated into or through the septum and the one or more of the closure or the shaft is in the second position opening the at least one port;
   moving one or more of the first connector portion or the second connector portion relative to each other from the closed position toward the open position;
   piercing the septum with the piercing member and at least partially penetrating into or through the septum with the at least one port;
   moving one or more of the closure or the shaft from the first position, closing the at least one port, to the second position, opening the at least one port;
   introducing fluid from or into the shaft through the at least one port; and
   during the piercing step, substantially preventing any contact between the at least one port and the septum.

71. A method as defined in claim 70, further including withdrawing the piercing member from the septum;
   before or during the withdrawing step, moving one or more of the closure or the shaft from the second position to the first position, such that the at least one port is in the closed position and sealed with respect to ambient atmosphere;
   moving the one or more of the first connector portion or the second connector portion relative to each other from the open position to the closed position;
   disengaging the first connector portion with the second connector portion; and
   during the withdrawing step, substantially preventing any contact between the at least one port and the septum.

72. An apparatus comprising:
   a first device including a piercing member comprising a hollow shaft, a piercing tip formed at one end of the shaft, at least one port in fluid communication with an interior of the hollow shaft, and a closure that receives only a portion of the piercing member including the at least one port; wherein one or more of the closure or the shaft is movable between (i) a first position wherein the closure closes the at least one port, and (ii) a second position opening the at least one port;
   a second device adapted for engagement with the first device and including a pierceable septum configured to be pierced by the piercing member when the piercing member engages the septum;
   wherein one or more of the first device or the device is moveable relative to each other between (i) a closed position wherein the at least one port has at least partially penetrated into or through the septum and the one or more of the closure or the shaft is in the first position and closes the at least one port and (ii) an open position wherein the at least one port has at least partially penetrated into or through the septum and the one or more of the closure or the shaft is in the second position opening the at least one port, and
   wherein the septum is configured to wipe contaminants from the piercing member during movement of one of the first device and the second device relative to the other.

73. A connector as in claim 72, wherein said wiping achieves at least approximately a 3 log reduction in bio-burden.

74. A method comprising:
   engaging a first device with a second device,
      the first device comprising a piercing member including a hollow shaft, a piercing tip formed at one end of the shaft, at least one port in fluid communication with an interior of the hollow shaft, and a closure that receives only a portion of the piercing member including the at least one port; wherein one or more of the closure or the shaft is movable between (i) a first position wherein the closure closes the at least one port, and (ii) a second position opening the at least one port;
      the second device is adapted for engagement with the first device and including a pierceable septum configured to be pierced by the piercing member when the piercing member engages the septum;
      and one or more of the first device or the second device is moveable relative to each other between (i) a closed position wherein the at least one port has at least partially penetrated into or through the septum and the one or more of the closure or the shaft is in the first position and closes the at least one port and (ii) an open position wherein the at least one port has at least partially penetrated into or through the septum and the one or more of the closure or the shaft is in the second position opening the at least one port;
   moving one or more of the first device or the second device relative to each other from the closed position toward the open position;

piercing the septum with the piercing member, at least partially penetrating into or through the septum with the at least one port, and, during said piercing, wiping contaminants from the piercing member with the septum;

moving one or more of the closure or the shaft from the first position, closing the at least one port, to the second position, opening the at least one port; and introducing fluid from or into the shaft through the at least one port.

* * * * *